United States Patent [19]
Thomas et al.

[11] Patent Number: 5,904,698
[45] Date of Patent: May 18, 1999

[54] SURGICAL SHAVING DEVICE FOR USE WITHIN BODY CONDUITS

[75] Inventors: Thomas P. Thomas, Menlo Park; Charles C. Hart, Huntington Beach; Said Hilal, Laguna Niguel, all of Calif.

[73] Assignee: Applied Medical Resources Corporation, Laguna Hills, Calif.

[21] Appl. No.: 08/872,206

[22] Filed: Jun. 10, 1997

[51] Int. Cl.[6] .................................................. A61B 17/22
[52] U.S. Cl. .......................................... 606/159; 606/194
[58] Field of Search .................................. 606/159, 194, 606/200; 604/93, 96, 267, 266; 607/122

[56] References Cited

U.S. PATENT DOCUMENTS

| | | | |
|---|---|---|---|
| 4,650,466 | 3/1987 | Luther | 604/95 |
| 4,919,133 | 4/1990 | Chiang | 606/159 |
| 5,100,423 | 3/1992 | Fearnot | 606/159 |
| 5,496,267 | 3/1996 | Drasler | 604/22 |
| 5,527,282 | 6/1996 | Segal | 604/104 |
| 5,540,707 | 7/1996 | Ressemann et al. | 606/159 |
| 5,569,276 | 10/1996 | Jang et al. | 606/159 |
| 5,578,007 | 11/1996 | Imran | 604/95 |

*Primary Examiner*—Michael Buiz
*Assistant Examiner*—Julian W. Woo
*Attorney, Agent, or Firm*—Richard L. Myers

[57] ABSTRACT

A surgical device is disclosed for treating and removing obstructing material from within a vascular conduit or other body passageway. The device comprises a catheter device having an expandable and collapsible outer mesh sleeve disposed at a distal end. The outer mesh sleeve is configured such that when expanded in the obstructed conduit or passageway, a portion of the obstructing material is forced through a plurality of openings in its outer surface and thus, into the outer mesh sleeve. An inflatable and deflatable balloon may be coupled to the catheter and used to radially expand the outer mesh sleeve into the obstructing material. A treatment element disposed within the catheter device is moved against the inner surface of the outer mesh sleeve to treat and remove any obstructing material with which it contacts. The treatment element may be configured as a blade for physically removing the obstructing material, or as an electrode for electrosurgical treatment. After treatment or removal of the obstructing material, the outer mesh sleeve is collapsed and the catheter device removed from the body conduit.

27 Claims, 4 Drawing Sheets

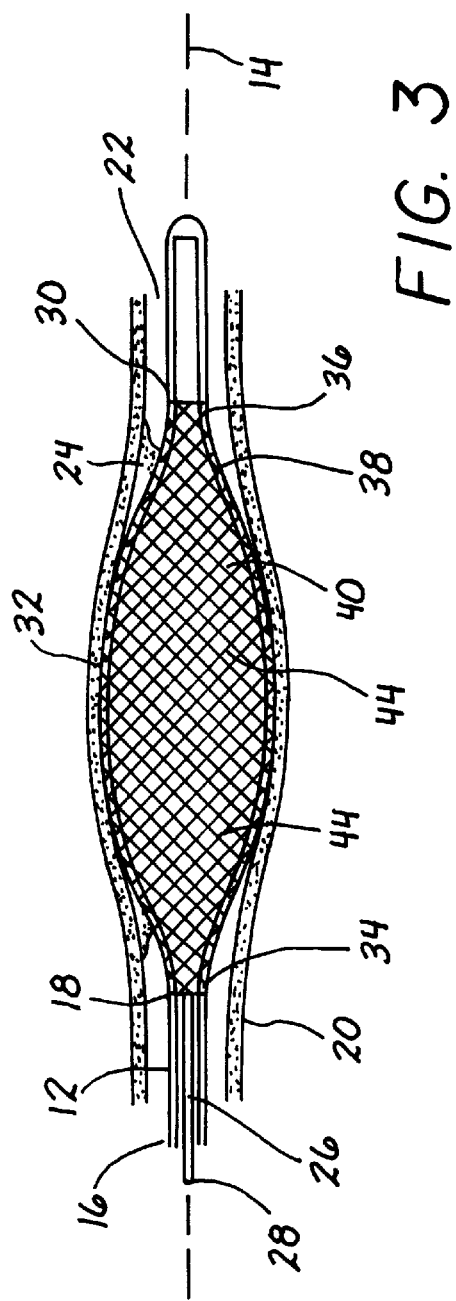
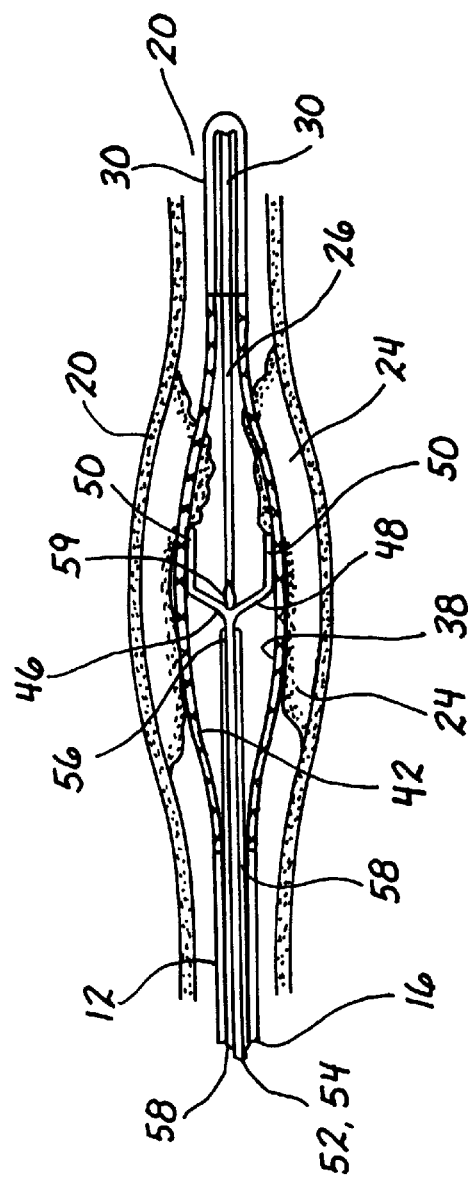

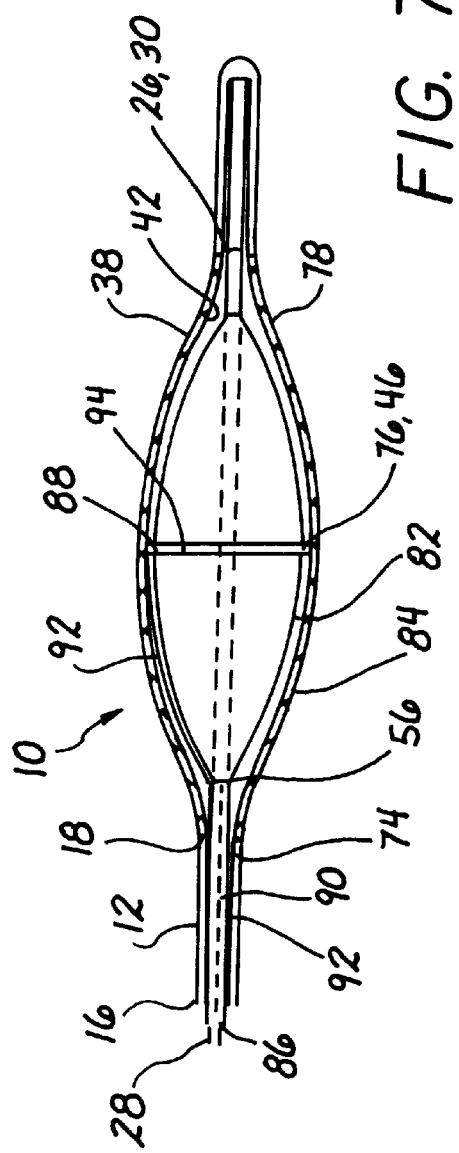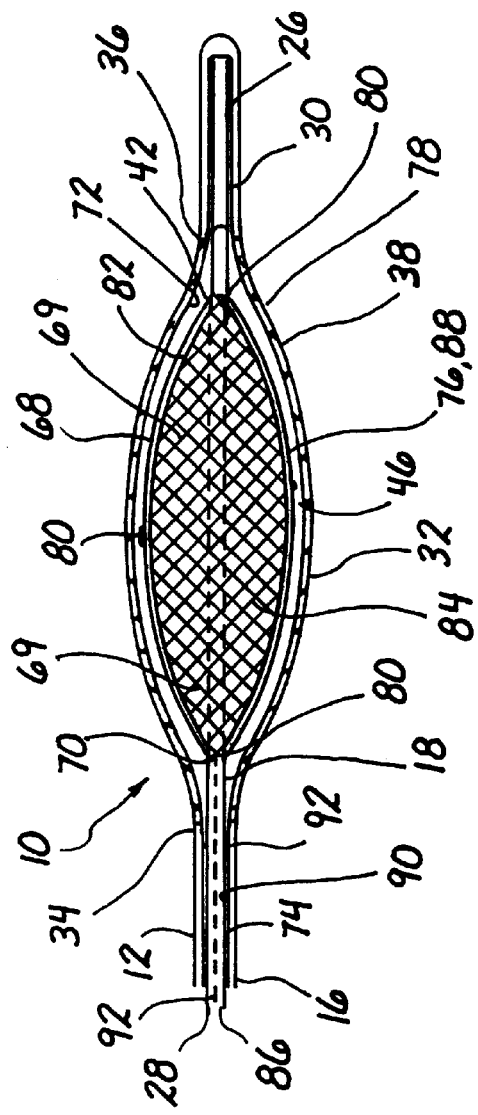

SURGICAL SHAVING DEVICE FOR USE WITHIN BODY CONDUITS

FIELD OF THE INVENTION

This invention relates generally to devices and methods for use in vascular conduits and other body passageways and more particularly, to an expandable surgical catheter device and method for clearing obstructions within a vascular conduit or other body passageway.

BACKGROUND OF THE INVENTION

The human body contains a great number of tubular vessels and conduits through which flow a variety of physiological fluids. These tubular vessels and conduits include the vascular system, the urological system, the intestinal system, as well as other body conduits. Flow through these conduits may be restricted by obstructions or other reductions in the flow passageway. For example, a vascular obstruction in the form of deposits or growths in a patient's artery or vein may restrict or stop blood flow to a certain portion of the patient's body. As a second example, an obstruction in the urethra due to an enlarged prostate may restrict the passage of fluids through the urethral canal. This may be particularly serious if such an obstruction occurs in a portion of the vascular system or other body conduit that supplies vital organs with blood or other necessary fluids. Obstructions, must therefore, be removed quickly while minimizing trauma, discomfort and other negative impacts on the patient.

A number of different therapies are available for the treatment and removal of obstructing material from a vessel or other body conduit. Notably, balloon angioplasty and mechanical atherectomy have evolved as the two principal surgical procedures for the treatment of obstructions within the vascular system.

Balloon angioplasty comprises a procedure wherein a deflated balloon is introduced, by means of a catheter, to the obstructed area within the vessel or other body conduit. The balloon is then inflated to open the lumen or passageway of the conduit. The inflated balloon tends to crush or compact the obstructing material against the conduit wall as well as to crack the obstructing material and dilate the conduit so as to increase the patency of the conduit.

While balloon angioplasty is quite successful in substantially opening the lumen within certain vessels and conduits, it does not remove the obstructing material. Since this obstructing material is not removed, there is a significant possibility that the conduit will become re-occluded or re-obstructed at the treated area within a relatively short period of time. This re-occlusion generally requires another treatment to reopen the lumen.

The balloon angioplasty procedure has several additional drawbacks which tend to further reduce its desirability. For instance, in the case of a severely occluded vessel, it may be difficult to position the deflated balloon so that it spans the occlusion without causing undue trauma to the surrounding vessels. In addition, the balloon angioplasty procedure is not satisfactory for treating calcified and hard occlusions, which are more difficult to crack and dilate. Similarly, balloon angioplasty is not satisfactory for treating eccentric occlusions since the balloon tends to simply stretch the healthy vascular tissue without compressing the occluding material.

In contrast to balloon angioplasty, atherectomy procedures are diverted toward the removal of obstructing material from within the body conduit. These treatment devices use a variety of means to remove the obstructing material. For example, rotating cutters, abraders and lasers may be used. The rotating cutters may be particularly useful in removing certain types of vascular obstructions. In particular, since vascular obstructions may have different compositions and shapes, a given removal or cutting element may not be suitable for the removal of a particular obstruction. Alternatively, if a patient has multiple obstructions within a vessel, a given removal element may be suitable for removing only one of the obstructions. The cutting, grinding and abrading devices also have a tendency to perforate the wall of the vessel or conduit. This is of particular concern in curved sections of the vessel or conduit.

Based on these considerations, it is apparent that the need remains for a surgical device which can effectively remove obstructing material from within a vessel, a urethral canal, or other body conduit without perforating or otherwise damaging the conduit. There is also a need for such a surgical device which may be used to remove differing obstructing material from within various body conduits, each having a different diameter, curvature, or other configuration. There is also a need for such a device which is simple to use and inexpensive to manufacture.

SUMMARY OF THE INVENTION

The present invention overcomes these problems of the past by providing a surgical device which is capable of treating and removing obstructing material from within a vessel or other body conduit. By using a surgical device which is insertable into the obstructed conduit and which includes a removal blade and a thin mesh outer sleeve for a blade stop, obstructing material can be removed without perforating or otherwise damaging the body conduit. In addition, the use of an outer sleeve which is independently expandable into a number of differing radial configuration, allows the present surgical device to be used within a plurality of different vessels and conduits. The surgical device of the present invention is thus, capable of conforming to a plurality of different vessels and body conduits without requiring a change of removal tips, blades or even different surgical devices.

The present invention also satisfies the need for a surgical device which can remove obstructing material within a vascular conduit, a urological conduit, or other types of body passageways. By using an outer mesh sleeve which can be expanded and collapsed into a number of predetermined diameters and shapes, the surgical device of the present invention may be used within conduits having differing diameters and configurations. In addition, by providing a plurality of different treatment elements, the surgical device can effectively remove obstructing materials of differing compositions and configurations.

The present invention is generally directed to a surgical device for removing obstructing material and enlarging a flow passageway within a vascular or urological conduit, or other body passageway. The device includes a hollow catheter having a longitudinal axis extending between a proximal end and a distal end. The catheter is configured for insertion and manipulation within the vascular or urological conduit, or other body passageway.

A radially expandable and collapsible outer sleeve is coupled to the catheter adjacent the distal end. A plurality of openings extend between an outer surface and an inner surface of the sleeve. The outer sleeve is adapted such that it may be radially expanded against and into the obstructing material thereby causing discrete portions of the obstructing material to protrude into the outer sleeve through the openings.

A treatment element is disposed within the outer sleeve and adapted for the treatment and removal of the obstruction portions which protrudes into the outer sleeve. The treatment element is coupled to the distal end of a shaft which extends generally longitudinally within the catheter tube. The shaft is axially and radially movable within the catheter tube in order to bring the treatment element into contact with the inner surface of the outer sleeve. In this way, movement of the treatment element against the inner surface of the outer sleeve contacts and treats the portion of obstructing material which extends within the inner surface.

The present invention contemplates a variety of differing treatment elements. In one embodiment, the treatment element is a blade which is moved across the inner surface of the outer sleeve to cut the obstructing material. The blade may be made from a piece or pieces of flat spring material such that it expands and collapses with the outer sleeve.

In another embodiment of the present invention, the treatment element is an electrode. In this aspect, the electrode is moved across the inner surface of the expandable sleeve and desiccates or otherwise removes the obstructing material which protrudes within the inner surface of the outer sleeve. The surgical device may comprise a monopolar configuration wherein the electrode (treatment element) is charged as a probe and the patient comprises a second or return electrode. Alternatively, the surgical device may incorporate a bi-polar configuration, wherein the electrode (treatment element) is charged as a probe and the outer sleeve comprises the second or return electrode. In this configuration, the treatment element includes a non-electrically conductive distal end or spacer which prevents an electrical short or discharge between the first electrode and the second electrode.

In another aspect of the present invention, the outer sleeve has a mesh configuration. The outer mesh sleeve is made from a plurality of filaments which are woven to produce a plurality of openings or interstices. The filaments may be made from a material which is electrically non-conductive, for use with a mono-polar configuration, or alternatively, from a material which is electrically conductive, for use in a bi-polar configuration.

In yet another embodiment of the present invention, the surgical device includes a hollow catheter tube having a longitudinal axis which extends between a proximal end and a distal end. An inner member longitudinally slidable within the catheter tube also includes a proximal end and distal end. An outer mesh sleeve surrounds a distal portion of the inner member and includes a plurality of mesh openings. The outer mesh sleeve has a proximal sleeve end which is coupled to the distal end of the catheter tube and a distal sleeve end which is coupled adjacent the distal end of the inner member.

In this embodiment, the outer mesh sleeve is radially expandable and collapsible through longitudinal movement of the inner member relative to the catheter tube. This allows the outer mesh sleeve to be radially expanded such that its outer mesh surface is forced against the obstructing material and a portion of the obstructing material is forced into the mesh openings. A treatment element is disposed within the outer mesh sleeve and adapted for movement against the inner surface such that the obstructing material which extends into the outer mesh sleeve is contacted and treated by the treatment element.

An inflatable and deflatable balloon is disposed within the outer mesh sleeve. The balloon is used to radially expand the outer mesh sleeve within the body conduit and into the obstructing material. The balloon is inflated until the outer mesh sleeve is expanded and forced into the obstructing material. The balloon is then deflated so that the treatment element may be moved across the inner surface to treat the obstructing material which protrudes into the outer mesh sleeve.

The treatment element may be moved over the partially deflated or fully deflated balloon. The treatment element may include a blade which slides over the balloon for mechanically removing any obstructing material which protrudes into the outer mesh sleeve. Alternatively, the treatment element may be a wire electrode which moves over the outer surface of the balloon.

In another aspect of the present embodiment, a second wire mesh sleeve is disposed around the exterior surface of the balloon but within the outer sleeve. In this configuration, the second mesh sleeve acts as the treatment element and may be radially expanded against the inner surface of the outer sleeve. Movement of the second mesh sleeve relative to the outer sleeve removes any obstructing material which protrudes through the outer mesh sleeve.

In an alternative aspect of the above configuration, the second mesh sleeve may comprise an electrode. In this configuration, the second mesh sleeve is made from an electrically conductive material and is electrically coupled to the second shaft or other electrical conductor which in turn is connected to an electrosurgical generator.

In yet another alternative configuration, the balloon may be fitted with an electrically conductive coating which functions as an electrode. This second electrode may be configured for contacting the inner surface of the outer sleeve as previously discussed.

A preferred method for enlarging a flow passageway and treating an obstructing material within a body conduit according to the principles of the present invention, comprises the steps of providing a surgical catheter device having a radially expandable and collapsible outer mesh sleeve and an internal treatment element, and moving the element against an inner surface of the outer mesh sleeve.

The catheter device is directed within the body conduit and moved adjacent the obstructing material. The outer mesh sleeve is radially expanded out and against the obstructing material so that the mesh sleeve is pushed into the obstructing material and at least a portion of the obstructing material is forced through a plurality of openings in the outer mesh sleeve. The treatment element is then moved across the inner surface of the mesh sleeve such that the portion of obstructing material which protrudes into the outer mesh sleeve is contacted and treated by the treatment element. After treatment, the expanded outer mesh sleeve is collapsed and the catheter device is removed from the body conduit.

In another aspect of the present invention, the method includes the steps of inflating a balloon, which is incorporated within the outer mesh sleeve, to radially expand the outer mesh sleeve and force it into the obstructing material. Once the outer mesh sleeve is expanded sufficiently that a portion of the obstructing material protrudes through some of the mesh openings, the balloon is deflated to expose an inner surface on the outer mesh sleeve. The treatment element may then be moved within the outer mesh sleeve to contact and treat the obstructing material.

This invention, together with the additional features and advantages thereof, which is only summarized in the foregoing passages, will become more apparent to those of skill in the art upon reading the description of the preferred embodiments, which follows in the specification, taken together with the following drawings.

BRIEF DESCRIPTION OF THE DRAWINGS

FIG. 3 is an axial cross-sectional view of the surgical device of FIG. 1 shown in a fully expanded configuration;

FIG. 4 is an axial cross-sectional view of an embodiment of the surgical device of the present invention showing a treatment element having a double blade configuration;

FIG. 7 is an axial cross-sectional view of an alternative embodiment of the surgical device of the present invention shown having an internal balloon and an electrode for a treatment element; and FIG. 8 is an axial cross-sectional view of the surgical device of FIG. 7 shown having a second mesh sleeve surrounding the balloon.

DESCRIPTION OF THE PREFERRED EMBODIMENTS

Figure 1:
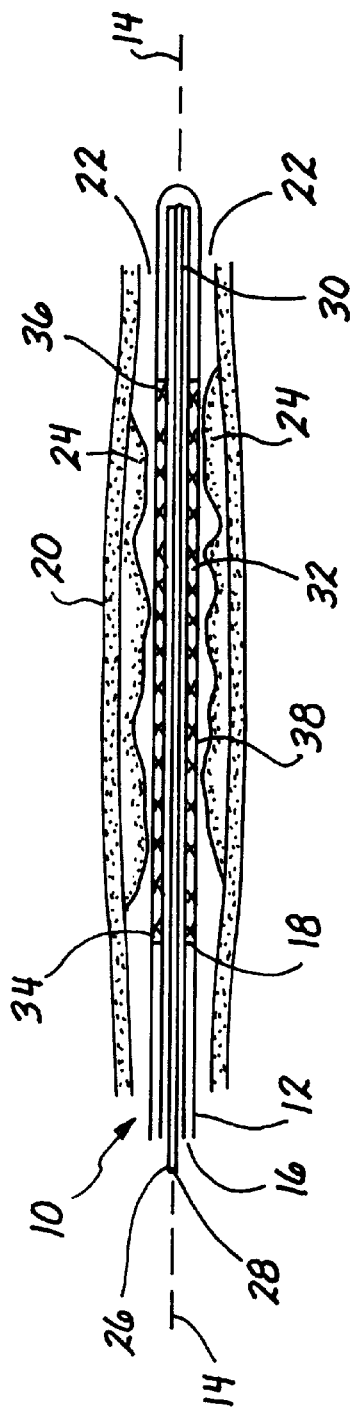
FIG. 1 is an axial cross-sectional view of an embodiment of the surgical device having an outer mesh sleeve disposed within a body conduit illustrated in a collapsed configuration.

Referring now to the drawings, wherein like reference characters designate identical or corresponding parts throughout the several views and embodiments, a surgical device according to the present invention is illustrated in FIG. 1 and designated by the reference numeral 10.

As shown in FIG. 1, the surgical device 10 is insertable within a body conduit 20 having a lumen or flow passageway 22 which has been narrowed or partially blocked by an obstructing material 24. The body conduit 20 may also be a vessel, such as an artery or vein which has become narrowed or occluded through the formation of plaque, thrombus, clots, polyps, or any other obstructing material 24. The body conduit 20 may also include a previously stented vessel that has experienced hyperplasia, resulting in a reduced flow passageway 22, or even a complete occlusion.

In yet another alternative application, the body conduit 20 may comprise a urethra which has become narrowed due to benign prostate hyperplasia. Another application includes the treatment of polyps from within the intestinal tract. The surgical device 10 of the present invention may be used to treat obstructing material 24 within most any body conduit 20 whose flow passageway has been narrowed or otherwise obstructed.

Figure 2:
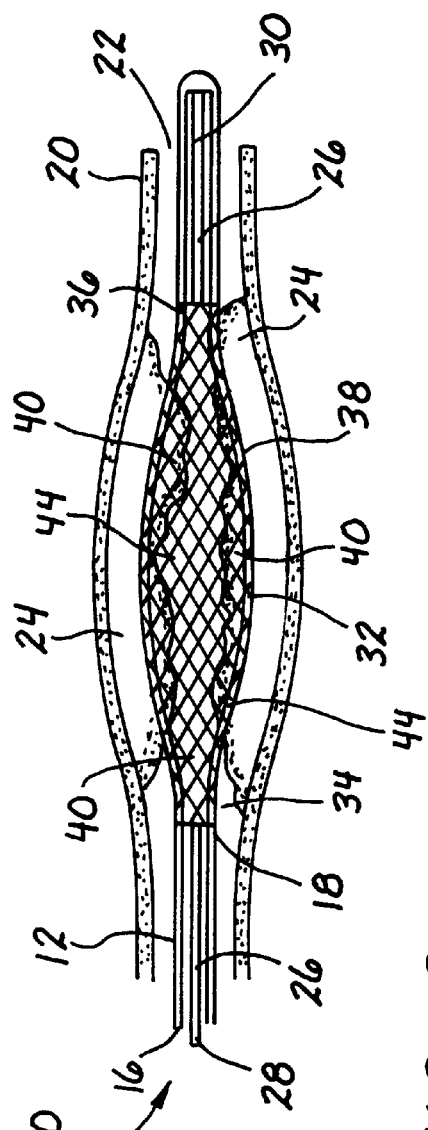
FIG. 2 is an axial cross-sectional view of the surgical device of FIG. 1 shown in a partially expanded configuration.

As shown in FIGS. 1 through 3, the surgical device includes an elongate catheter tube 12 having a longitudinal axis 14 which extends between a proximal end 16 and a distal end 18. An elongate inner member 26 may be provided within the catheter 12 which also extends along, or adjacent to, the longitudinal axis 14. The inner member 26 includes a proximal end 28 and a distal end 30. As will be discussed in greater detail later, the inner member 26 may consist of a tube, a rod, or even a guidewire, having a slightly smaller cross-section or diameter than the catheter tube 12.

An outer sleeve 32 is disposed in a generally coaxial configuration about the inner member 26. The outer sleeve includes a proximal sleeve end 34 and a distal sleeve end 36. Preferably, the proximal sleeve end 34 is connected to the distal end 18 of the catheter tube 12 and the distal sleeve end 36 is connected adjacent the distal end 30 of the inner member 26. The outer sleeve ends 34 and 36 may be bonded, fused, clamped, or otherwise securely attached to the respective catheter tube 12 and inner member 26, to insure a structurally secure connection.

The outer sleeve 32 may be made from a material that is expandable and collapsible. Preferably, the outer sleeve 32 is radially expandable and collapsible between a fully collapsed configuration, best illustrated in FIG. 1, and a fully expanded configuration, best illustrated in FIG. 3. The outer sleeve 32 may also be configured for movement into a number of partially expanded configurations (FIG. 2). The expanding and collapsing of the outer sleeve 32 may be achieved through longitudinal movement of the inner member 26 relative to the catheter tube 12, in a manner described in greater detail below.

The outer sleeve 32 may be made from a thin tubular material having a plurality of openings 40 which extend between an exterior or outer surface 38 and an inner surface 42. Preferably, the outer sleeve 32 comprises a woven mesh sleeve made from a filament or plurality of filaments 44. The filaments 44 may be cross-helically wound, braided or otherwise woven into fingers which define a multiplicity of interstices or openings 40 which are expandable or collapsible when the inner member 26 is moved longitudinally relative to the catheter tube 12.

Individual filaments 44 may be specifically sized and cross-sectionally shaped to advantageously configure the outer sleeve 32. For example, the filament 44 may have a round cross-section to provide for a relatively smooth outer surface 38, or rectangular in-cross section, including a sharp edge, to provide a relatively abrasive or tractive outer surface 38. Increasing the diameter of the filament 44 may also be used to increase the abrasiveness or tactiveness of the outer mesh sleeve 32. In this way, the outer mesh sleeve 32 may be formed with a smooth or even an abrasive or tractive outer surface 38.

As mentioned, when the inner member 26 is moved longitudinally relative to the catheter tube 12, the outer sleeve 32 is also forced to move. For example, distal movement of the inner member 26 relative to the catheter tube 12 elongates the outer sleeve 32 and radially collapses or otherwise reduces the diameter of the outer sleeve 32. The collapsed or maximum elongated length of the outer sleeve 32 may be used to limit the maximum distal movement of the inner member 26 relative to the catheter tube 12. Alternatively, proximal longitudinal movement of the inner member 26, which shortens the distance between the distal ends 18 and 30 of the inner member 26 and the catheter tube 12, respectively, forces the outward bulging or radial expansion of the outer sleeve 32. This radial expansion of the outer sleeve 32 is preferably sufficient such that the outer sleeve 32 can be moved radially outward to contact the inner walls of the body conduit 20.

An actuating mechanism (not shown) may be coupled to the catheter tube 12 and the inner member 26 to facilitate their relative movement. This actuating mechanism may include any apparatus and method of operation, such as a handle or other grip, for actuating a catheter or similar device as is known to those of skill in the art.

A treatment element 46 may be disposed within the outer sleeve 32. The treatment element 46 is preferably adapted and configured for movement along and against the inner surface 42 of the outer sleeve 32. In this way, obstructing material 24 which protrudes through the plurality of openings 40 and into the outer sleeve 32 may be contacted and treated by the treatment element 46. Preferably, each of the plurality of openings 40 is sufficiently large that a maximum amount of obstructing material 24 protrudes therethrough while the treatment element 46 is sized such that it does not penetrate through or become entangled within any of the plurality of openings 40. The treatment element 46 may also be configured such that it may not extend or protrude beyond the outer surface 38 of the outer sleeve 32, thus, preventing damage to the body conduit 20.

Referring now to FIG. 4, the treatment element 46 may comprise a mechanical blade 48 for physically removing any obstructing material 24 which protrudes into the outer sleeve 32. In this configuration, the inner surface 42 acts as a blade screen, similar to a common electric face shaver, and prevents removal or damage to any tissue not protruding into the outer sleeve 32. The blade 48 may have a plurality of blade tips 50 which are moved across and along the entire inner surface 42. This movement may include rotating the blade 48 radially, for example, about the axis 14, while moving the blade 48 longitudinally along the inner surface 42.

Preferably, a shaft 52 having a proximal shaft end 54 and a distal shaft end 56 extends through the catheter tube 12. The treatment element 46 may be coupled to the distal shaft end 56. In this way, the shaft 52 may be used to drive and otherwise control the treatment element 46. A sheath 58 may be provided around a substantial portion of the shaft 52. The sheath 58 generally extends through the catheter tube 12 and may be fixedly attached thereto. Preferably, the shaft 52 is longitudinally slidable and rotatable within the sheath 58. In this configuration, the sheath 58 may comprise a naturally lubricating surface or alteratively may be provided with a lubricant.

The treatment element 46 is preferably configured for being radially expanded and collapsed along with the outer sleeve 32. Thus, the treatment element 46 may comprise a blade 48 having a sharp tip 50 or alternatively, a plurality of tips 50 which are normally parallel to the longitudinal axis 14 when the outer sleeve 32 is in the collapsed configuration, as best illustrated in FIG. 1. Alternatively, by distally extending the shaft 52 within the shaft sheath 58, the treatment element 46 can be extended within the outer sleeve 32 to expose the blade tips 50. These tips 50, which may be made from a spring metal, a wire, a hard plastic, or any other suitable material, and may have a sharp flat edge, are radially expandable to contact the inner surface 42 of the outer sleeve 32. Thus, movement of the shaft 52 distally within the catheter 12 continues to further expose the treatment element 46, and expand the blade tips 50 until they contact the inner surface 42.

A spring or similar device 59 may be used to assist in maintaining the blade tip or blade tips 50 outwardly and away from the longitudinal axis 14 and against the inner surface 42. For example, a spring 59 may be mounted between each of the blade tips 50 as shown in FIG. 4.

Figure 5:
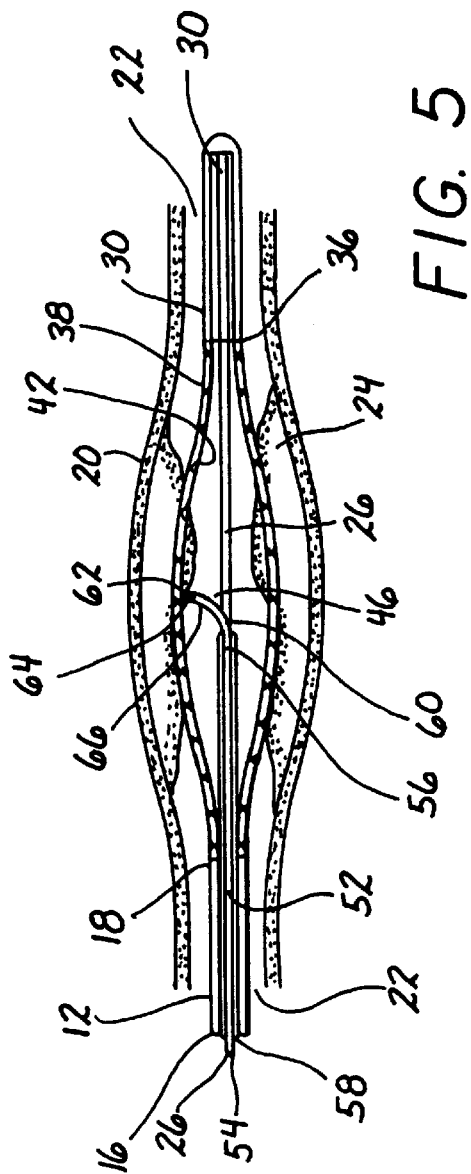
FIG. 5 is an axial cross-sectional view similar to FIG. 4 and illustrating an electrode for a treatment element.

Referring now to FIG. 5, the treatment element 46 may also comprise an electrode 60 as shown. In this configuration, the electrode 60 may be electrically charged using an electrosurgical generator or similar device, and moved along the inner surface 42 of the expanded outer sleeve 32 for contact with any obstructing material 24 which protrudes through the plurality of openings 40 and into the outer sleeve 32. In this configuration, the surgical device 10 generally operates as an electrosurgical shaver.

The electrode 60, which may be in the form of an electrosurgical wire or wires 61, may have a mono-polar or bi-polar configuration. In a mono-polar configuration, the outer sleeve 32 would be typically made from an electrically non-conductive material. Thus, the filaments 44 may comprise a non-conductive plastic or other material. The body conduit 20, or preferably the patient, may then be connected to the electrosurgical generator as the return electrode.

The non-conducting inner surface 42 acts as a stopper, which prevents the electrode 60 from reaching and damaging any tissue which does not protrude within the plurality of openings 40. In the mono-polar configuration, the electrode 60 may comprise an electrosurgical wire or wires. The electrode 60 may be configured similarly to the blade 48 to prevent its movement through the plurality of openings 40 such that tissue which does not protrude into the outer sleeve 32 is left untreated. In this configuration, the electrode 60 may be radially expanded and collapsed along with the outer sleeve 32 through longitudinal movement of the interconnected shaft 52 within the shaft sheath 58. The shaft 52 may be made from an electrically conductive material, such as a wire, and electrically coupled to the electrosurgical generator to energize to the electrode 60. The shaft sheath 58 may be an insulator to shield the conducting shaft 52.

In a bi-polar configuration, the electrode 60 may be used to carry an electrical charge from the electrosurgical generator and the outer sleeve 32 may be used to carry a return or second charge. In this configuration, the treatment element 46 may comprise a first electrode 60 and the outer sleeve 32 may comprise a second electrode. The treatment element 46 is preferably configured as a probe 62 made from an electrosurgical wire, and may include an electrically non-conducting spacer 64 on its distal end 66. The non-conducting spacer 64 maintains a gap between the probe 62 and the outer sleeve 32 to prevent unwanted electrical discharge between the first electrode 60 or probe 62 and the second electrode or outer sleeve 32. Any tissue trapped between the energized probe 62 and the inner surface 42 of the outer sleeve 32 would be contacted by the probe 62, desiccated and eventually destroyed.

After conclusion of the treatment, the outer sleeve 32 may be released from the catheter 12 and inner member 26, and left within the body conduit 20 as a stent for supporting the conduit. In this configuration, the outer sleeve 32 must be releasably connected to the catheter 12 and the inner member 26.

Figure 6:
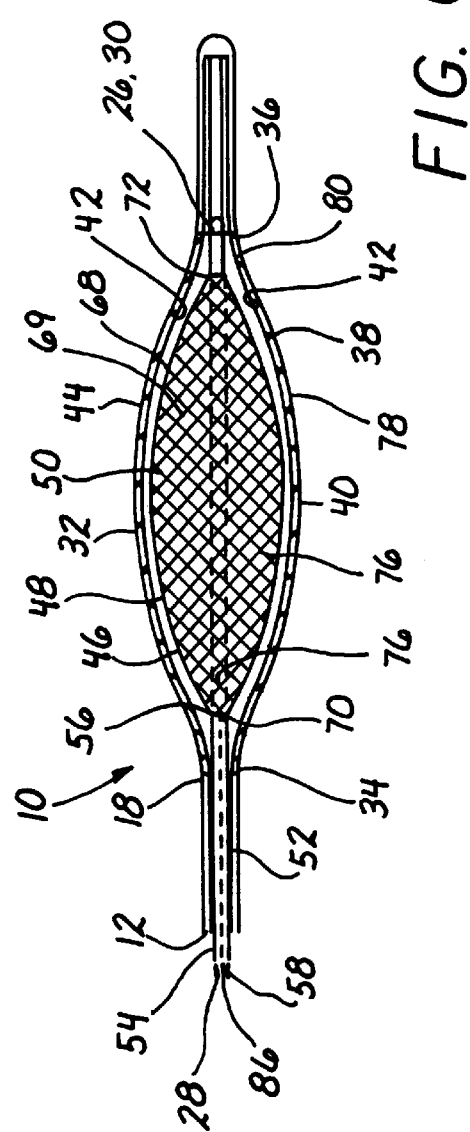
FIG. 6 is an axial cross-sectional view of the surgical device of FIG. 3 shown having a second mesh sleeve for a treatment element.

The treatment element 46 may also comprise a second, or inner mesh sleeve 68, as shown in FIG. 6. In this embodiment, the treatment element 46 may be an inner mesh sleeve 68 consisting of filaments 69 arranged in a similar configuration to that described for the outer sleeve 32. With this construction, the sleeve is expandable and collapsible in a similar way as the outer sleeve 32. The inner mesh sleeve 68 may be fitted within and surrounded by the outer sleeve 32. In this configuration, the inner mesh sleeve 68 comprises a proximal inner sleeve end 70 which may be connected to the distal shaft end 56. A distal inner sleeve end 72 is connected to a second treatment shaft 74 which extends longitudinally along, or preferably within hollow first treatment shaft 52. Longitudinal movement of the second treatment shaft 74 relative to the first shaft 52 forces the inner mesh sleeve 68 to radially expand and collapse as it is shortened and elongated.

The first treatment shaft 52 and the second treatment shaft 74 may also be coupled with the previously described actuating mechanism such that the outer sleeve 32 and the inner mesh sleeve 68 are radially expanded and collapsed at a similar rate. Alternatively, a second actuating mechanism may be provided which allows for the radial expanding and collapsing of the inner mesh sleeve 68 within the previously expanded outer sleeve 32. The actuating mechanism may also include a separate mechanism for rotating or otherwise moving the first shaft 52 such that the inner mesh sleeve 68 is movable relative to the outer sleeve 32.

The inner mesh sleeve 68 may be used as a mechanical blade for physically removing obstructing material 24 which protrudes through the plurality of openings 40 and into the outer sleeve 32, or alternatively, may be electrically charged to function as an electrode. When used as a mechanical blade, the outer sleeve 32 is radially expanded into the obstructing material 24 such that a portion of the obstructing material 24 protrudes through the plurality of the openings 40 and into the outer sleeve 32. The inner mesh sleeve 68, which also includes a plurality of openings or meshes, is radially expanded against the inner surface 42 of the outer sleeve 32 such that a portion of the obstructing material 24 which extends within the outer sleeve 32 also protrudes within the openings in the inner mesh sleeve 68.

The inner mesh sleeve 68 may then be rotated or otherwise moved relative to the outer sleeve 32, such that the filaments 69 of the inner mesh sleeve 68 contact and remove the obstructing material 24 which protrudes into the outer sleeve 32. Collapsing of the inner mesh sleeve 68 acts to retain any shaved or otherwise removed material 24, so that it may be withdrawn and taken from within the body conduit 20.

The inner mesh sleeve 68 may also be electrically charged to function as a first electrode 76. In a mono-polar configuration, similar to that previously described, the body conduit 20 or alternatively the patient, would be connected to an electrosurgical generator or similar device and act as a return or second electrode 78.

In a bi-polar configuration, the inner mesh sleeve 68 would be electrically charged as the first electrode 76 and the outer sleeve 32 would be interconnected as the return or second electrode 78. A spacer 80, made from a non-conducting material, such as a plastic or other insulator, may be placed between the inner mesh sleeve 68 and the outer sleeve 32 to prevent electrical discharging therebetween. Preferably, the spacer 80, which may be a plurality of spacers or contact points, is fitted on the inner mesh sleeve 68 and may also act as a friction reducing surface or bearing for contact with the inner surface 42 of the outer sleeve 32.

Referring now to FIGS. 7 and 8, a balloon 82 may be disposed about the inner member 26 to define an inflatable and deflatable annular balloon chamber 84. The balloon 82 may be made from a distensible material or a non-distensible material to provide characteristics well known to those of skill in the art.

The balloon 82 may be connected around the inner member 26 in a variety of fashions and configurations. Preferably, the inner member 26 is a tubular member and includes an internal longitudinal passageway 86 which is fluidly connected with the annular balloon chamber 84. In this way, a fluid may be passed through the internal longitudinal passageway 86 to inflate, or alternatively, to deflate the balloon 82.

Preferably, the balloon 82 is disposed within the outer sleeve 32 such that the balloon 82 may be used to radially expand the outer sleeve 32. The balloon 82 may also be used to merely assist in the radial expansion of the outer sleeve 32. Similarly, the deflation of the balloon 82 may be used to collapse the outer sleeve 32. Use of the balloon 82 advantageously allows radial expansion of the outer sleeve 32 to a plurality of different diameters. In addition, the balloon 82 may be inflated to force the outer sleeve 32 into the obstructing material 24.

Preferably, the outer sleeve 32, which may be a mesh sleeve as previously described, is radially expanded such that it contacts the obstructing material 24. The balloon 82 may then be inflated such that it contacts the inner surface 42 and pushes or forces the filaments 44, including the plurality of openings 40, into the obstructing material 24. The outer sleeve 32 may be expandable to a maximum radial diameter. In this configuration, the balloon 82 is advantageously prevented from being overinflated so as to overdilate the body conduit 20.

Preferably, the treatment element 46 is disposed between the balloon 82 and the inner surface 42 of the outer sleeve 32. In this way, inflation of the balloon 82 may be used to move the treatment element 46 against the inner surface 42. When used with a balloon 82, the treatment element 46 is preferably an inner mesh sleeve 68 which is radially expanded and collapsed with the inflated and deflated balloon 82. The inner mesh sleeve 68 may then be interconnected with the electrosurgical generator or similar device as previously described.

In an alternative configuration, the treatment element 46 may comprise an electrode 88, similar to that previously discussed, which is movable within a tubular sheath 90. The electrode 88 or other treatment element 46 may be configured such that it is longitudinally extendable and movable along the outer surface of the balloon 82. A shaft 92, which may be an electrosurgical wire, extends longitudinally through the catheter tube 12 and is coupled to the electrode 88. The shaft 92 may be configured as part of the inner member 26. Alternatively, the tubular sheath 90 may take the place of the inner member 26.

In yet another alternative configuration, the treatment element 46 may be a mechanical blade 94 as previously described. The blade 94 is preferably movable along the outer surface of the balloon 82 and against the inner surface 42 of the outer sleeve 32. The blade 94 may be interconnected with the shaft 92 as previously described.

It will be understood that various modifications can be made to the various embodiments herein disclosed, without departing from the spirit and scope of the invention. For example, various sizes of the surgical device and particularly, the outer sleeve are contemplated as well as various types of construction materials. Also, various modifications may be made in the configuration of the parts and their interaction. Therefore, the above description should not be construed as limiting the invention, but merely as an exemplification of preferred embodiments thereof. Those of skill in the art will envision other modifications within the scope and spirit of the present invention as defined by the claims appended hereto.

What is claimed is:

1. A surgical device for treating an obstructing material within a body conduit, the surgical device comprising:

a hollow catheter for insertion into said body conduit, said catheter having a longitudinal axis extending between a proximal end and a distal end;

a radially expandable and collapsible woven mesh outer sleeve having a plurality of openings extending from an outer surface through to an inner surface, said outer sleeve coupled to said catheter adjacent said distal end and adapted for radially expanding against said obstructing material such that portions of said obstructing material are forced to protrude through said openings and into said outer sleeve;

a shaft extending longitudinally within said catheter tube, said shaft movable within said catheter tube and having a proximal shaft end and a distal shaft end; and a treatment element disposed within said outer sleeve and connected to the distal shaft end, said treatment element adapted for movement against the inner surface of said outer sleeve to treat the portions of the obstructing material which extend within the inner surface of the outer sleeve.

2. The surgical device as recited in claim 1 wherein said treatment element comprises a blade.

3. A surgical device for treating an obstructing material within a body conduit, the surgical device comprising:

a hollow catheter for insertion into said body conduit, said catheter having a longitudinal axis extending between a proximal end and a distal end;

a radially expandable and collapsible outer sleeve having a plurality of openings extending from an outer surface through to an inner surface, said outer sleeve coupled to said catheter adjacent said distal end and adapted for radially expanding against said obstructing material such that portions of said obstructing material are forced to protrude through said openings and into said outer sleeve;

a shaft extending longitudinally within said catheter tube, said shaft movable within said catheter tube and having a proximal shaft end and a distal shaft end; and a treatment element in the form of a radially expandable and collapsible inner mesh sleeve disposed within said outer sleeve and connected to the distal shaft end, said treatment element adapted for movement against the inner surface of said outer sleeve to treat the portions of the obstructing material which extend within the inner surface of the outer sleeve.

4. The surgical device as recited in claim 3 wherein said outer mesh sleeve comprises woven filaments made from an electrically non-conducting material.

5. The surgical device as recited in claim 4 wherein said treatment element further comprises a non-electrically non-conductive distal end for preventing an electrical short between said first electrode and said second electrode.

6. A surgical device for treating an obstructing material within a body conduit, the surgical device comprising:

a hollow catheter for insertion into said body conduit, said catheter having a longitudinal axis extending between a proximal end and a distal end;

a radially expandable and collapsible outer sleeve having a plurality of openings extending from an outer surface through to an inner surface, said outer sleeve coupled to said catheter adjacent said distal end and adapted for radially expanding against said obstructing material such that portions of said obstructing material are forced to protrude through said openings and into said outer sleeve;

a shaft extending longitudinally within said catheter tube, said shaft movable within said catheter tube and having a proximal shaft end and a distal shaft end; and a treatment element in the form of an electrode disposed within said outer sleeve and connected to the distal shaft end, said treatment element adapted for movement against the inner surface of said outer sleeve to treat the portions of the obstructing material which extend within the inner surface of the outer sleeve.

7. A surgical device for treating an obstructing material within a body conduit, the surgical device comprising:

a hollow catheter for insertion into said body conduit, said catheter having a longitudinal axis extending between a proximal end and a distal end;

a radially expandable and collapsible outer sleeve having a plurality of openings extending from an outer surface through to an inner surface, said outer sleeve coupled to said catheter adjacent said distal end and adapted for radially expanding against said obstructing material such that portions of said obstructing material are forced to protrude through said openings and into said outer sleeve;

a shaft extending longitudinally within said catheter tube, said shaft movable within said catheter tube and having a proximal shaft end and a distal shaft end;

a treatment element in the form of disposed within said outer sleeve and connected to the distal shaft end, said treatment element adapted for movement against the inner surface of said outer sleeve to treat the portions of the obstructing material which extend within the inner surface of the outer sleeve; wherein said treatment element comprises a first electrode and said outer mesh sleeve comprises a second electrode.

8. A surgical device for treating an obstructing material within a flow passageway of a body conduit, the surgical device comprising:

a hollow catheter tube adapted for insertion into said body conduit, said catheter tube having a longitudinal axis extending between a proximal end and a distal end;

an inner member extending longitudinally through said catheter tube and including a proximal end and a distal end, said inner member being longitudinally slidable within said catheter tube;

an outer mesh sleeve surrounding a distal portion of said inner member and having a plurality of mesh openings extending from an outer surface of the sleeve to an inner surface of the sleeve, said outer mesh sleeve having a proximal sleeve end coupled to said distal end of said catheter tube and a distal sleeve end coupled to said distal end of said inner member such that said outer mesh sleeve is radially expandable and collapsible through longitudinal movement of said inner member relative to said catheter tube, and wherein said outer mesh sleeve is radially expandable such that the outer mesh surface may be forced against said obstructing material such that a portion of said obstructing material is forced to protrude through at least one of said mesh openings and into said outer mesh sleeve; and a treatment element disposed within said outer mesh sleeve, said treatment element adapted for movement against the inner surface of said outer mesh sleeve such that the portion of the obstructing material which extends into said outer mesh sleeve is contacted and treated by said treatment element.

9. The surgical device as recited in claim 8, and further comprising an inflatable and deflatable balloon disposed within said outer mesh sleeve for expanding said outer mesh sleeve into said obstructing material.

10. The surgical device as recited in claim 9 wherein said balloon is inflatable such that it radially expands sufficiently to force said treatment element against said inner surface.

11. The surgical device as recited in claim 9 further comprising a second inner member extending longitudinally within said catheter tube, said second inner member being hollow and having a distal end connected to said balloon, said second inner member being fluidly connected with said balloon such that said balloon is inflatable and deflatable.

12. The surgical device as recited in claim 11 wherein said inner member and said second inner member are the same.

13. The surgical device as recited in claim 8, and further comprising a shaft connected to said treatment element and being longitudinally movable to slide said treatment element against the inner surface of said outer mesh sleeve.

14. The surgical device as recited in claim 8 wherein said treatment element is a blade.

15. The surgical device as recited in claim 8 wherein said treatment element is an inner mesh sleeve.

16. The surgical device as recited in claim 8 wherein said treatment element is a first electrode.

17. The surgical device as recited in claim 16 wherein said first electrode is an electrosurgical wire.

18. The surgical device as recited in claim 17 wherein said treatment element further comprises an electrically non-conductive distal end for preventing electrical discharging between said first electrode and said second electrode.

19. The surgical device as recited in claim 16 wherein said first electrode is an inner mesh sleeve.

20. The surgical device as recited in claim 16 wherein said outer mesh sleeve comprises a material which is electrically non-conductive.

21. The surgical device as recited in claim 8 wherein said treatment element comprises a first electrode and said outer mesh sleeve comprises a second electrode.

22. The surgical device as recited in claim 8, and further comprising an actuating mechanism for moving said inner member longitudinally relative to said catheter tube.

23. A method for enlarging a flow passageway and treating an obstructing material within a body conduit, said method comprising the steps of:

providing a catheter device having a radially expandable and collapsible outer mesh sleeve and an internal electrode which is movable against an inner surface of the outer mesh sleeve;

directing the catheter device within the body conduit and adjacent the obstructing material;

expanding the outer mesh sleeve against the obstructing material such that the mesh sleeve is forced into the obstructing material and at least a portion of the obstructing material is forced through a plurality of openings in the mesh sleeve;

moving the electrode against the inner surface of the mesh sleeve such that the portion of the obstructing material which protrudes into the outer mesh sleeve is contacted and treated by the treatment element;

collapsing the expanded outer mesh sleeve; and removing the catheter device from the body conduit.

24. A method for enlarging a flow passageway and treating an obstructing material within a body conduit, said method comprising the steps of:

providing a catheter device having a radially expandable and collapsible outer mesh sleeve and an internal treatment element which is movable against an inner surface of the outer mesh sleeve;

directing the catheter device within the body conduit and adjacent the obstructing material;

expanding the outer mesh sleeve against the obstructing material such that the mesh sleeve is forced into the obstructing material and at least a portion of the obstructing material is forced through a plurality of openings in the mesh sleeve;

during the expanding step, inflating a balloon disposed within the outer mesh sleeve to radially expand the outer mesh sleeve and embed the outer mesh in the obstructing material, and deflating said balloon while leaving the outer mesh sleeve embedded in the obstructing material;

moving the treatment element against the inner surface of the mesh sleeve such that the portion of the obstructing material which protrudes into the outer mesh sleeve is contacted and treated by the treatment element;

collapsing the expanded outer mesh sleeve; and removing the catheter device from the body conduit.

25. A method for treating an obstructing material and enlarging a flow passageway within a vascular conduit supported by a stent, said method comprising the steps of:

providing a catheter device having a radially expandable and collapsible outer sleeve and a live electrode disposed within the outer sleeve for movement against an inner surface of the outer sleeve and for treatment of any obstructing material which protrudes through a plurality of openings in the outer sleeve;

directing the catheter device within the vascular passageway such that the outer sleeve is within the stent and adjacent the obstructing material;

expanding the outer sleeve against the obstructing material such that the outer sleeve is forced into the obstructing material and at least a portion of the obstructing material is forced through the plurality of openings in the outer sleeve;

moving the live electrode against the inner surface of the outer sleeve such that the treatment element contacts and treats the portion of the obstructing material which is protruding through the outer sleeve; and removing the catheter device from the vascular passageway.

26. The method as recited in claim 25 wherein the step of moving comprises moving a blade against the inner surface of the outer sleeve for physically cutting the portion of the obstruction which is protruding into said outer sleeve.

27. A method for treating an obstructing material and enlarging a flow passageway within a vascular conduit supported by a stent, said method comprising the steps of:

providing a catheter device having a radially expandable and collapsible outer sleeve and a treatment element disposed within the outer sleeve for movement against an inner surface of the outer sleeve and for treatment of any obstructing material which protrudes through a plurality of openings in the outer sleeve;

directing the catheter device within the vascular passageway such that the outer sleeve is within the stent and adjacent the obstructing material;

expanding the outer sleeve against the obstructing material such that the outer sleeve is forced into the obstructing material and at least a portion of the obstructing material is forced through the plurality of openings in the outer sleeve;

during the expanding step, inflating a balloon disposed within said outer sleeve to radially expand said outer sleeve against said vascular conduit and into said obstructing material, and deflating said balloon to expose said inner surface of said outer sleeve;

moving the treatment element against the inner surface of the outer sleeve such that the treatment element contacts and treats the portion of the obstructing material which is protruding through the outer sleeve; and removing the catheter device from the vascular passageway.

* * * * *